United States Patent
Takeda et al.

(10) Patent No.: US 9,443,127 B2
(45) Date of Patent: Sep. 13, 2016

(54) CELL ANALYZING APPARATUS AND CELL ANALYZING METHOD

(71) Applicant: Nihon Kohden Corporation, Shinjuku-ku, Tokyo (JP)

(72) Inventors: Sunao Takeda, Tokyo (JP); Hirotsugu Kubo, Tokyo (JP); Takahiro Shioyama, Tokyo (JP); Akane Suzuki, Tokyo (JP); Kenichi Nomura, Tokyo (JP); Yo Kato, Tokyo (JP); Nae Hinata, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 0 days.

(21) Appl. No.: 14/488,947

(22) Filed: Sep. 17, 2014

(65) Prior Publication Data

US 2015/0078649 A1 Mar. 19, 2015

(30) Foreign Application Priority Data

Sep. 19, 2013 (JP) .................................. 2013-193949

(51) Int. Cl.
- *G06K 9/00* (2006.01)
- *G01N 21/64* (2006.01)
- *G01N 15/14* (2006.01)

(Continued)

(52) U.S. Cl.
CPC ....... *G06K 9/00127* (2013.01); *G01N 15/1429* (2013.01); *G01N 15/1459* (2013.01); *G01N 21/6428* (2013.01); *A61B 5/0071* (2013.01); *G01N 2015/1006* (2013.01); *G01N 2015/1402* (2013.01); *G01N 2015/1486* (2013.01);

(Continued)

(58) Field of Classification Search
CPC A61B 5/0071; A61B 1/00009; A61B 1/043; G06K 9/00127
See application file for complete search history.

(56) References Cited

U.S. PATENT DOCUMENTS

| | | | | |
|---|---|---|---|---|
| 5,018,209 A | * | 5/1991 | Bacus | G01N 15/1468 356/39 |
| 5,131,398 A | * | 7/1992 | Alfano | A61B 5/0071 600/476 |

(Continued)

FOREIGN PATENT DOCUMENTS

| | | |
|---|---|---|
| JP | 2012-047594 A | 3/2012 |
| WO | 2013015089 A1 | 1/2013 |

OTHER PUBLICATIONS

The Daily Dongle, FlowJo histogram overlay scaling options explained, Aug. 15, 2006, FlowJo for Windows and European Decimals, http://flowjo.typepad.com/the_daily_dongle/2006/08/flowjo_histogra.html.*

(Continued)

*Primary Examiner* — Stephen R Koziol
*Assistant Examiner* — Jonathan S Lee
(74) *Attorney, Agent, or Firm* — Sughrue Mion, PLLC

(57) ABSTRACT

A cell analyzing apparatus includes: a first histogram acquiring section which is configured to acquire a first histogram of fluorescence intensities by using a result of a measurement of a number of nuclear stained cells; a second histogram acquiring section which is configured to acquire a second histogram that is normalized based on a fluorescence intensity value indicating a maximum value of the first histogram; a determining section which is configured to determine whether cancer cells exist or not, based on one of the first histogram and the second histogram; and an outputting section which is configured to output a result of the determination performed by the determining section.

5 Claims, 6 Drawing Sheets

(51) Int. Cl.
*A61B 5/00* (2006.01)
*G01N 15/10* (2006.01)

(52) U.S. Cl.
CPC ............ *G01N2015/1488* (2013.01); *G01N 2021/6439* (2013.01)

(56) References Cited

U.S. PATENT DOCUMENTS

| | | | |
|---|---|---|---|
| 5,408,307 A * | 4/1995 | Yamamoto | G01N 15/1456 356/336 |
| 5,633,945 A * | 5/1997 | Kamentsky | 382/129 |
| 5,733,721 A * | 3/1998 | Hemstreet, III | G01N 33/574 382/133 |
| 8,208,142 B2 * | 6/2012 | Masilamani | G01N 33/57423 356/417 |
| 2003/0170703 A1 * | 9/2003 | Piper et al. | 435/6 |
| 2004/0042646 A1 | 3/2004 | MacAulay et al. | |
| 2012/0052491 A1 | 3/2012 | Shioyama et al. | |
| 2014/0030728 A1 * | 1/2014 | Shioyama et al. | 435/6.14 |
| 2014/0071328 A1 * | 3/2014 | Miesak | G03B 15/06 348/340 |

OTHER PUBLICATIONS

Parate, Ms Jayashree R., and R. K. Krishna. "Breast Cancer Detection Using Histogram Based Decomposition."*

Search Report dated Mar. 6, 2015, issued by the European Patent Office in counterpart European Application No. 14185334.1.

* cited by examiner

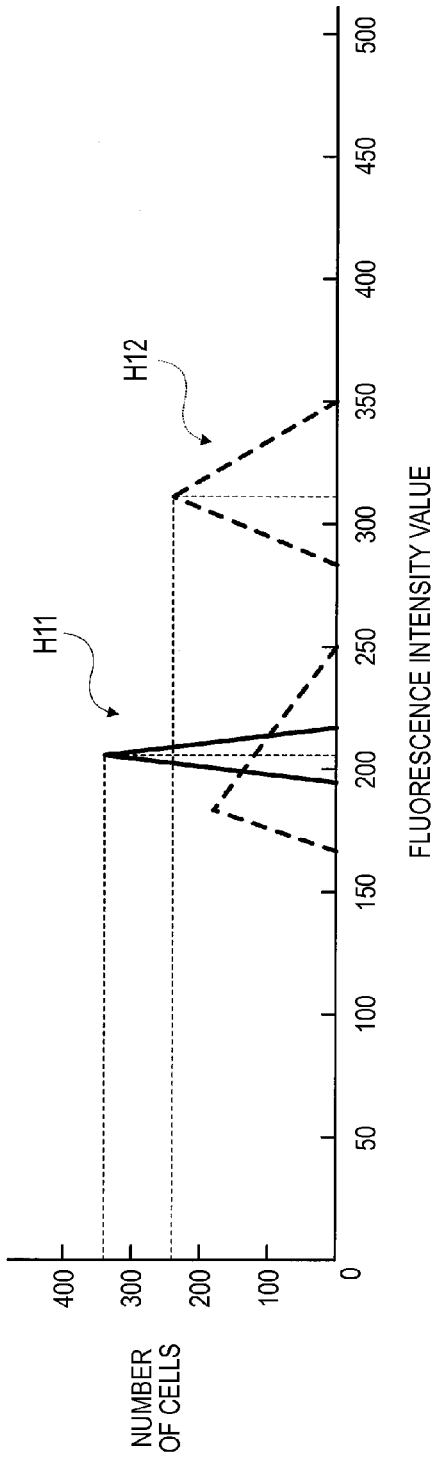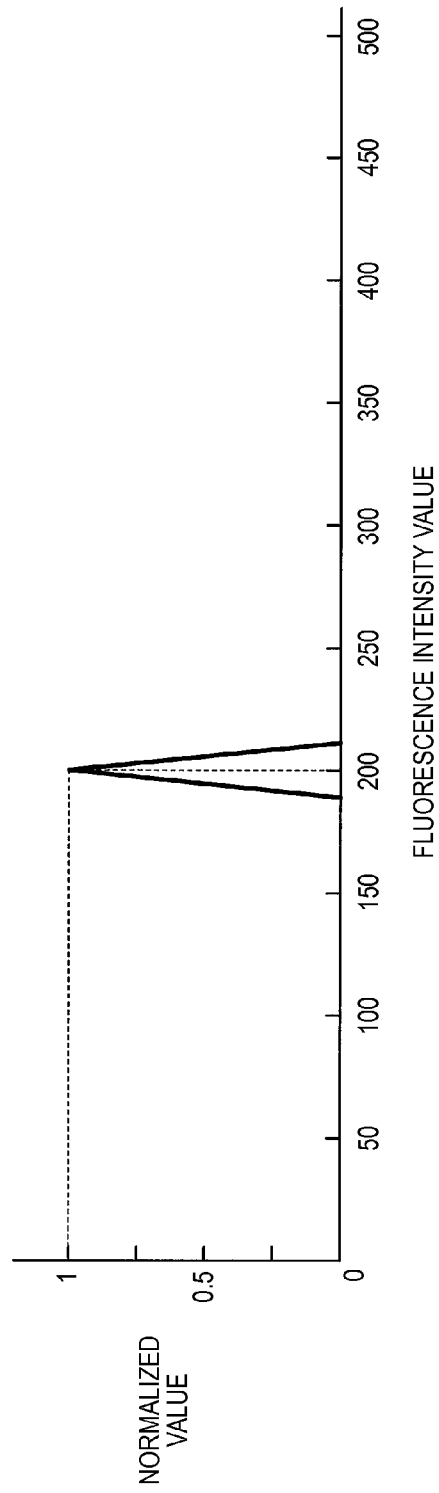

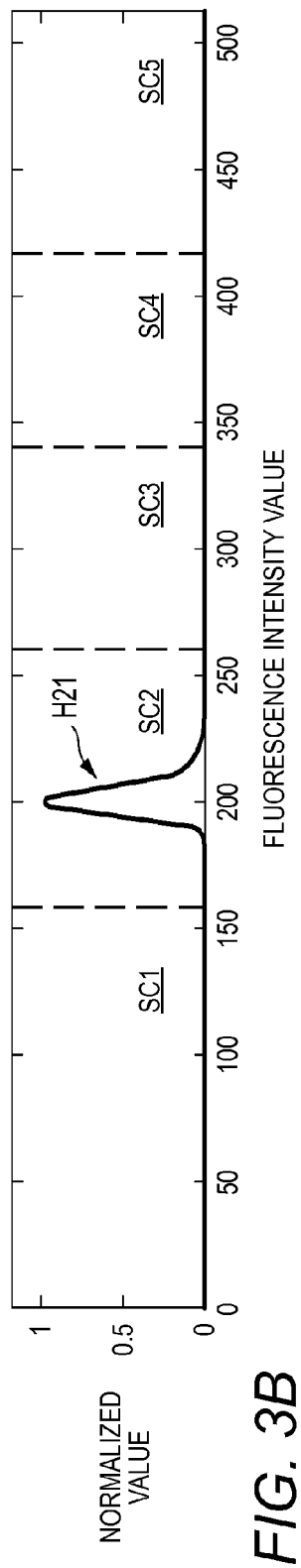
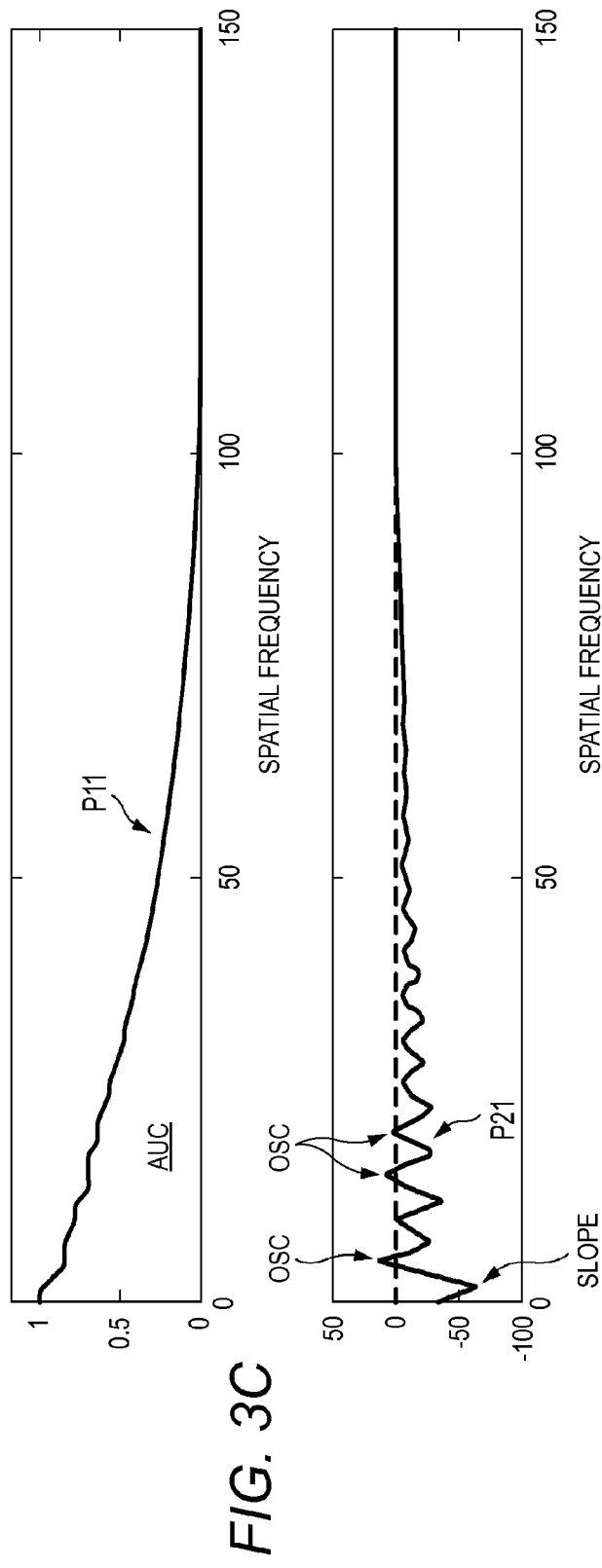
FIG. 3A
FIG. 3B
FIG. 3C

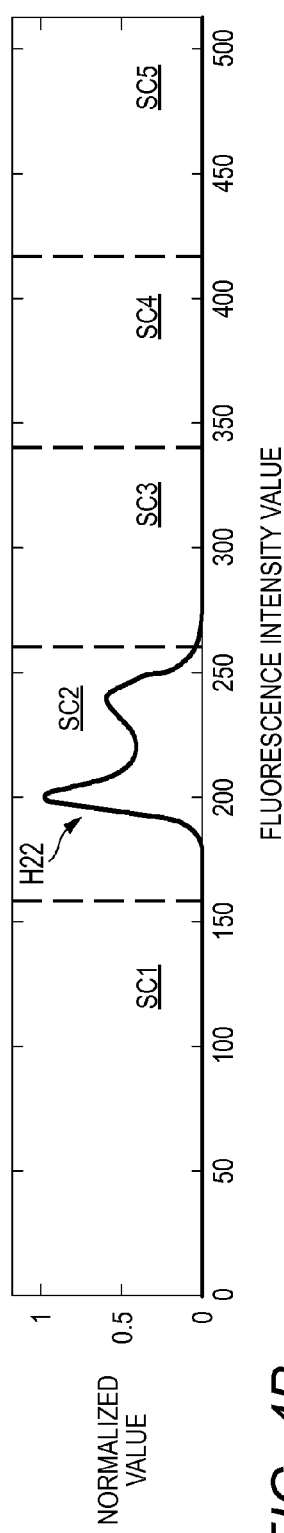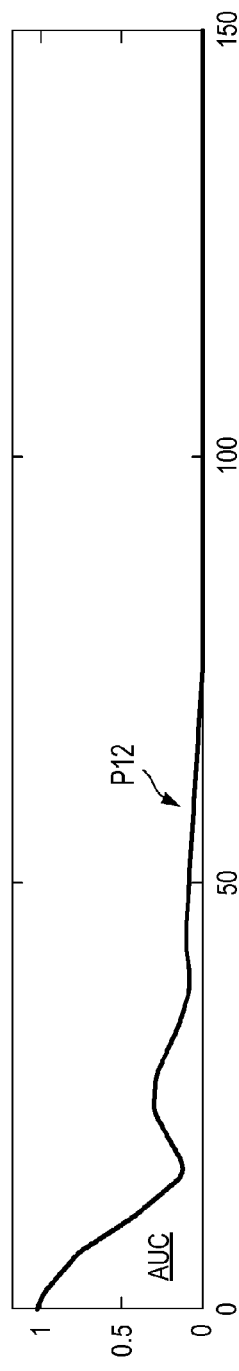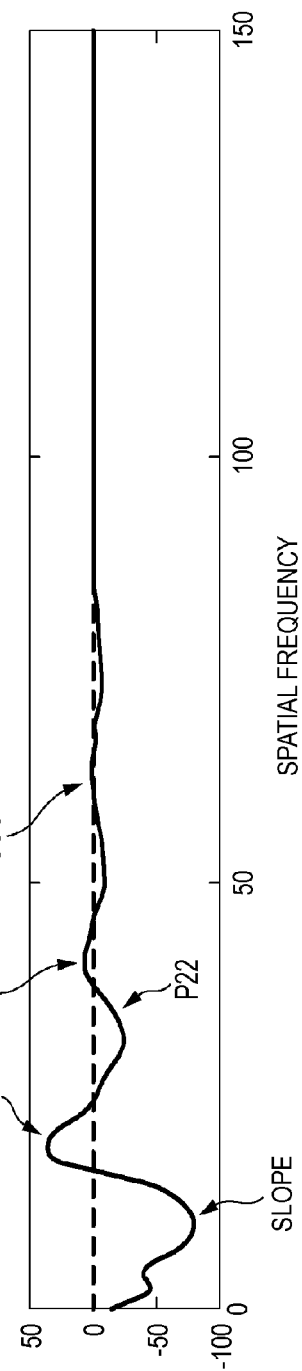

(12)  United States Patent
US 9,443,127 B2

CELL ANALYZING APPARATUS AND CELL ANALYZING METHOD

CROSS-REFERENCE TO RELATED APPLICATION(S)

This application is based upon and claims the benefit of priority from prior Japanese patent application No. 2013-193949, filed on Sep. 19, 2013, the entire contents of which are incorporated herein by reference.

BACKGROUND

The presently disclosed subject matter relates to a cell analyzing apparatus and a cell analyzing method which are used for distinguishing between normal and cancer tissues.

As an apparatus of this kind, there is an apparatus in which cells that are isolated and nuclear stained are measured, and a histogram of fluorescence intensities is acquired (for example, see JP-A-2012-47594). In the apparatus, the number of cells which are distributed in an area where the fluorescence intensity is stronger than that of normal cells is obtained from the acquired histogram, and the cancer malignancy grade is determined based on the number of cells and the histogram.

In order to minimize the extent of resection in surgery for removing cancer cells, it is requested to further improve the accuracy of identification of cancer cells.

SUMMARY

The presently disclosed subject matter may provide a technique for enabling cancer cells to be identified with higher accuracy.

There may be provided a cell analyzing apparatus comprising: a first histogram acquiring section which is configured to acquire a first histogram of fluorescence intensities by using a result of a measurement of a number of nuclear stained cells; a second histogram acquiring section which is configured to acquire a second histogram that is normalized based on a fluorescence intensity value indicating a maximum value of the first histogram; a determining section which is configured to determine whether cancer cells exist or not, based on one of the first histogram and the second histogram; and an outputting section which is configured to output a result of the determination performed by the determining section.

The determining section, in a case where the fluorescence intensity value indicating the maximum value of the first histogram is outside a predetermined range, may determine that the cancer cells exist, and, in a case where the fluorescence intensity value indicating the maximum value of the first histogram is within the predetermined range, may determine whether the cancer cells exist or not, based on the second histogram.

The cell analyzing apparatus may further comprise: an analyzing section which is configured to apply frequency analysis to the second histogram. The determining section may determine whether the cancer cells exist or not, based on a result of the frequency analysis.

The frequency analysis may include Fast Fourier Transform.

The determining section may divide fluorescence intensity values of the second histogram into a plurality of zones each of which corresponds to respective one of debris and a plurality of cancer cell cycles, and acquire an index relating to existence/nonexistence of the cancer cells for at least one of the plurality of zones, and fluorescence intensity values each of which corresponds to respective one of boundaries of the plurality of zones may be constant regardless of the acquired second histogram.

The determining section may acquire a plurality of indexes relating to existence/nonexistence of the cancer cells, based on a plurality of parameters relating to the second histogram, and determine whether the cancer cells exist or not, based on a combination of the plurality of indexes.

There also may be provided a cell analyzing method comprising: acquiring a first histogram of fluorescence intensities by using a result of a measurement of a number of nuclear stained cells; in a case where a fluorescence intensity value indicating a maximum value of the first histogram is outside a predetermined range, determining that cancer cells exist; in a case where the fluorescence intensity value indicating the maximum value of the first histogram is within the predetermined range, acquiring a second histogram that is normalized based on the fluorescence intensity value, and determining whether the cancer cells exist or not; and outputting a result of the determination.

BRIEF DESCRIPTION OF THE DRAWINGS

FIGS. 2A and 2B are views schematically showing acquisition of a second histogram by the cell analyzing apparatus.

FIGS. 3A to 3C are views showing an example of a frequency analysis applied to the second histogram.

FIGS. 4A to 4C are views showing another example of the frequency analysis applied to the second histogram.

DETAILED DESCRIPTION OF EXEMPLARY EMBODIMENTS

Hereinafter, an embodiment of the presently disclosed subject matter will be described in detail with reference to the accompanying drawings.

Figure 1:
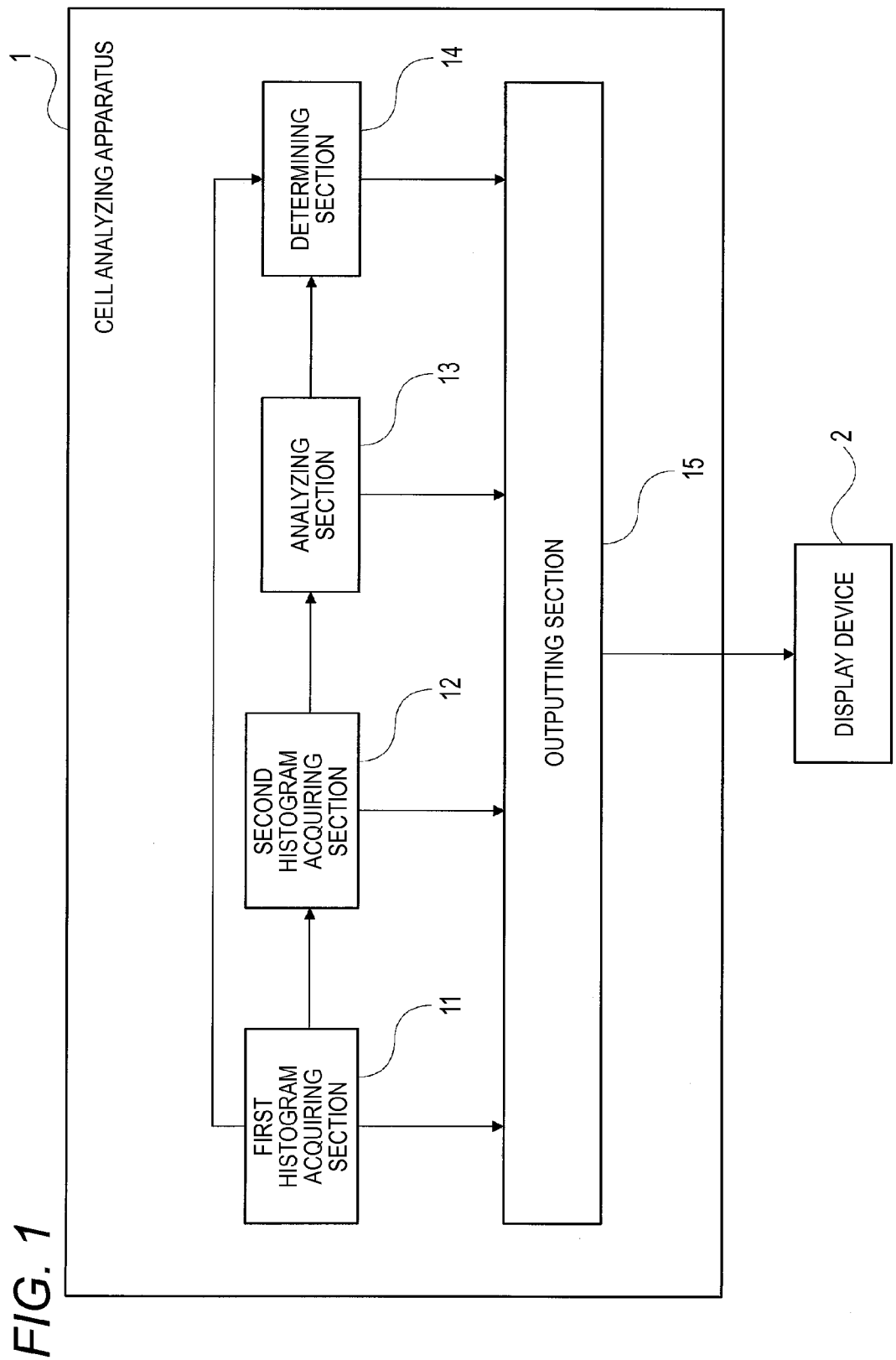
FIG. 1 is a block diagram showing the configuration of a cell analyzing apparatus of an embodiment of the presently disclosed subject matter.

FIG. 1 is a functional block diagram showing the configuration of a cell analyzing apparatus 1 of the embodiment of the presently disclosed subject matter. The cell analyzing apparatus 1 analyzes pre-processed tissue cells, and determines whether cancerous cells exist or not. The pre-process includes the cell isolation process by stirring or the like, nuclei isolation of tissue cells by a surfactant, RNA removal by an RNA remover, and staining of DNA cell nuclei by a fluorescent dye/pigment.

The cell analyzing apparatus 1 is connected to a display device 2. The cell analyzing apparatus 1 includes a first histogram acquiring section 11, a second histogram acquiring section 12, an analyzing section 13, a determining section 14, and an outputting section 15.

The first histogram acquiring section 11 performs flow cytometry. Specifically, a suspending solution in which isolated and nuclear stained cells are dispersed is irradiated with laser light. The cells contain fluorescent dye as a result of staining treatment, and exhibit different fluorescence intensities with respect to the laser light. The fluorescence intensity corresponds to the amount of dyes contained in DNA, and indicates the size of DNA.

In the flow cytometry, the number of calls for each value of the fluorescence intensity is measured. As a result, a first histogram shown in FIG. 2A is acquired. The abscissa of the first histogram indicates the value of the fluorescence intensity, and the ordinate indicates the number of cells. The shape of the first histogram is changed in accordance with the number of cells containing normal DNA, and that of cells containing cancerous DNA.

In FIG. 2A, a first histogram H11 acquired from tissue containing only normal cells is indicated by the solid line, and a first histogram H12 acquired from tissue containing cancer cells is indicated by the broken line. It is known that the first histogram acquired from normal cells has the maximum value (maximum cell number) in the range of the fluorescence intensity value of from 170 to 230. The numbers described herein are mere examples, and can be adequately changed according to set conditions of the apparatus or the like.

The determining section 14 performs a primary determination on the existence/nonexistence of cancer cells based on the first histogram acquired by the first histogram acquiring section 11. Specifically, if the maximum value of the first histogram is outside the range of the fluorescence intensity value of from 170 to 230 (an example of the predetermined range), it is immediately determined that cancer cells exist in the analysis object. Also the numbers described herein are mere examples, and can be adequately changed in a similar manner as described above.

In the case of the example shown in FIG. 2A, for example, the first histogram H12 indicated by the broken line has the maximum value in the vicinity of the fluorescence intensity value of 310. Therefore, the determining section 14 determines that the analysis object from which the first histogram H12 is acquired contains cancer cells.

If the determining section 14 determines that cancer cells exist, the outputting section 15 outputs a result of the determination to the display device 2. The display device 2 displays the determination result in an adequate manner such as characters, a symbol, or a color.

The second histogram acquiring section 12 acquires a second histogram which is normalized based on the fluorescence intensity value indicating the maximum value of the first histogram. The object of this process is a first histogram in which the maximum value is in the range of the fluorescence intensity value of from 170 to 230. Specifically, the second histogram is produced so that the fluorescence intensity value indicating the maximum value in the first histogram is normalized to 200, and the maximum value is normalized to 1. The numbers described herein are mere examples, and can be adequately changed.

In the example shown in FIG. 2A, for example, the first histogram H11 indicated by the solid line has the maximum value (about 320) in the vicinity of the fluorescence intensity value of 210. FIG. 2B shows a histogram which is obtained by normalizing the first histogram H11.

The analyzing section 13 performs frequency analysis including the Fast Fourier Transform on the second histogram acquired by the second histogram acquiring section 12.

FIG. 3A shows a second histogram H21 which is obtained from tissue containing only normal cells. FIG. 3B shows a pattern P11 which is acquired by performing the Fast Fourier Transform on the second histogram H21. FIG. 3C shows a differential pattern P21 which is acquired by differentiating the pattern P11. Also the acquisition of the differential pattern is an example of the frequency analysis.

FIG. 4A shows a second histogram H22 which is obtained from tissue containing cancer cells. FIG. 4B shows a pattern P12 which is acquired by performing the Fast Fourier Transform on the second histogram H22. FIG. 4C shows a differential pattern P22 which is acquired by differentiating the pattern P12.

The determining section 14 determines whether cancerous cells exist or not, based on the patterns and differential patterns (an example of the result of the frequency analysis) which are obtained by the frequency analysis performed by the analyzing section 13.

For example, an area under the curve (AUC) of a pattern which is obtained by performing the Fast Fourier Transform may be used as an index for the determination. When comparing the pattern P11 shown in FIG. 3B acquired from normal cells with the pattern P12 shown in FIG. 4B acquired from cancerous tissue, it is seen that the AUC value of the latter pattern is smaller. Therefore, the existence of cancer cells can be determined by the fact that the AUC value is smaller than a predetermined threshold.

In addition to or in place of the above, the maximum slope value (SLOPE) or distribution of minimal values (OSC) of the patterns obtained by the Fast Fourier Transform may be used as an index for the determination. The SLOPE can be obtained from the minimum value of the differential patterns obtained by the Fast Fourier Transform. The OSC can be obtained the distribution of maximal values (frequency bandwidths where maximal values exceeding a threshold exist) in the differential patterns.

When comparing the differential pattern P21 shown in FIG. 3C acquired from normal cells with the differential pattern P22 shown in FIG. 4C acquired from cancerous tissue, it is seen that the value of the SLOPE of the latter is smaller. Therefore, the existence of cancer cells can be determined by the fact that the value of the SLOPE is smaller than a predetermined threshold.

When comparing the differential pattern P21 shown in FIG. 3C acquired from normal cells with the differential pattern P22 shown in FIG. 4C acquired from cancerous tissue, it is seen that the value of the OSC of the latter is larger. Therefore, the existence of cancer cells can be determined by the fact that the value of the OSC is larger than a predetermined threshold.

As shown in FIGS. 3A and 4A, moreover, fluorescence intensity values of the second histogram are divided into a plurality of zones. The plurality of zones includes a first zone SC1, a second zone SC2, a third zone SC3, a fourth zone SC4, and a fifth zone SC5.

The first zone SC1 is a zone where debris, i.e., destroyed cells (dust) or interstitial tissue to which chromosomes adhere appear. The second zone SC2 is a zone where groups of G0/G1 phase cells, i.e., cells having a normal amount of DNA appear. The third zone SC3 is a zone where groups of S phase cells appear. The fourth zone SC4 is a zone where groups of G2/M phase cells appear. The fifth zone SC5 is a zone where cell groups having another amount of DNA appear.

Examples of indexes which can be acquired by such division into a plurality of zones are the total number of detected cells, the ratio of normal cells, the malignancy index, the ratio of debris, and the peak width of normal cells. The total number of detected cells indicates the total number of cells which appear in the first to fifth zones SC1 to SC5. The ratio of normal cells indicates a ratio of the number of cells appearing in the second zone SC2 to the total number of cells. The malignancy index indicates a ratio of the number of cells appearing in the third to fifth zones SC3 to SC5 to the total number of cells. The ratio of debris indicates a ratio of the number of cells appearing in the first zone to the total number of cells. The peak width of normal cells indicates the width of a peak waveform appearing in the second zone (for example, the width of a portion where the cell number is 5% or more of the maximum value). Thresholds for the indexes are determined by using the receiver operating characteristic (ROC) analysis or the like.

The determining section 14 determines whether cancerous cells exist or not, by using at least one of the above-listed indexes. The outputting section 15 outputs a result of the determination performed by the determining section 14 to the display device 2. The display device 2 displays the determination result in an adequate manner such as characters, a symbol, or a color.

Figure 5A:
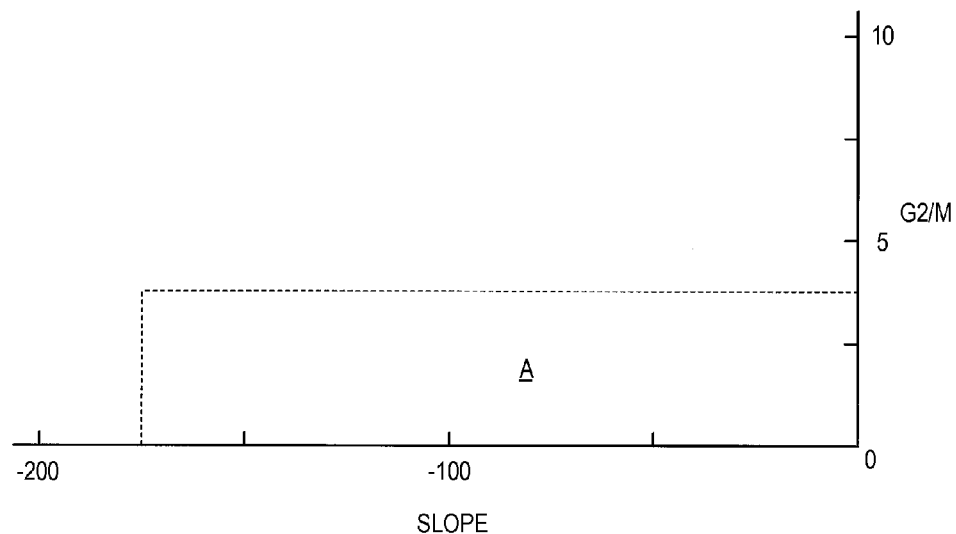
FIGS. 5A and 5B are views showing an example of determination of existence/nonexistence of cancer cells with using a plurality of indexes.
Figure 5B:
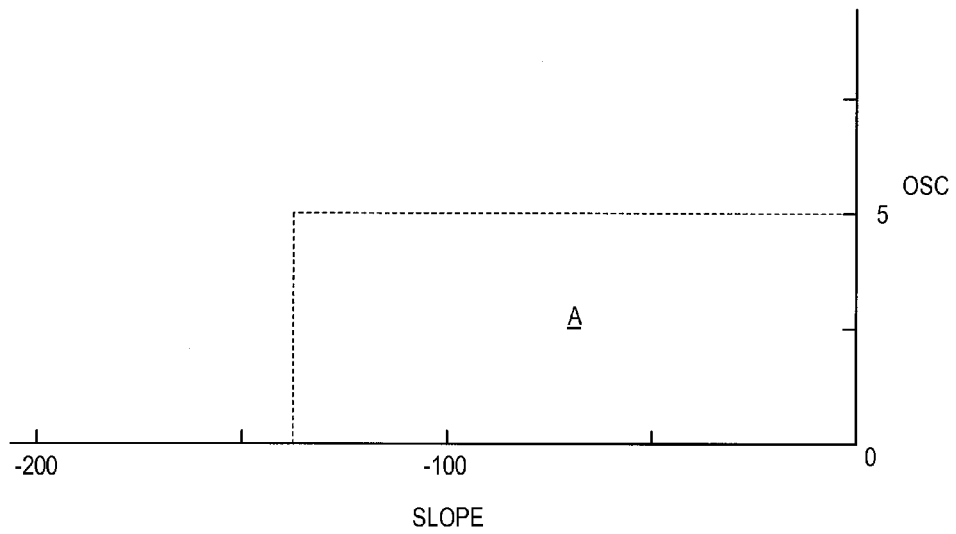

FIGS. 5A and 5B show examples in which the existence/nonexistence of cancer cells is determined by using a combination of a plurality of index. FIG. 5A shows an example in which the SLOPE and the G2/M (ratio of the number of cells appearing in the fourth zone SC4 to the total number of cells) were employed as indexes. FIG. 5B shows an example in which the SLOPE and the OSC were employed as indexes. The determining section 14 maps the data acquired by the analyzing section 13 onto a two-dimensional coordinate plane in which two indexes are used as the coordinate axes, and determines whether or not the data belong to a threshold region A that is determined by ROC analysis or the like.

If the data acquired by the analyzing section 13 belong to the threshold region A, the determining section 14 determines that the tissue to be analyzed contains cancer cells. The outputting section 15 outputs the result of the determination performed by the determining section 14 to the display device 2. The display device 2 displays the determination result in an adequate manner such as characters, a symbol, or a color.

Figure 6:
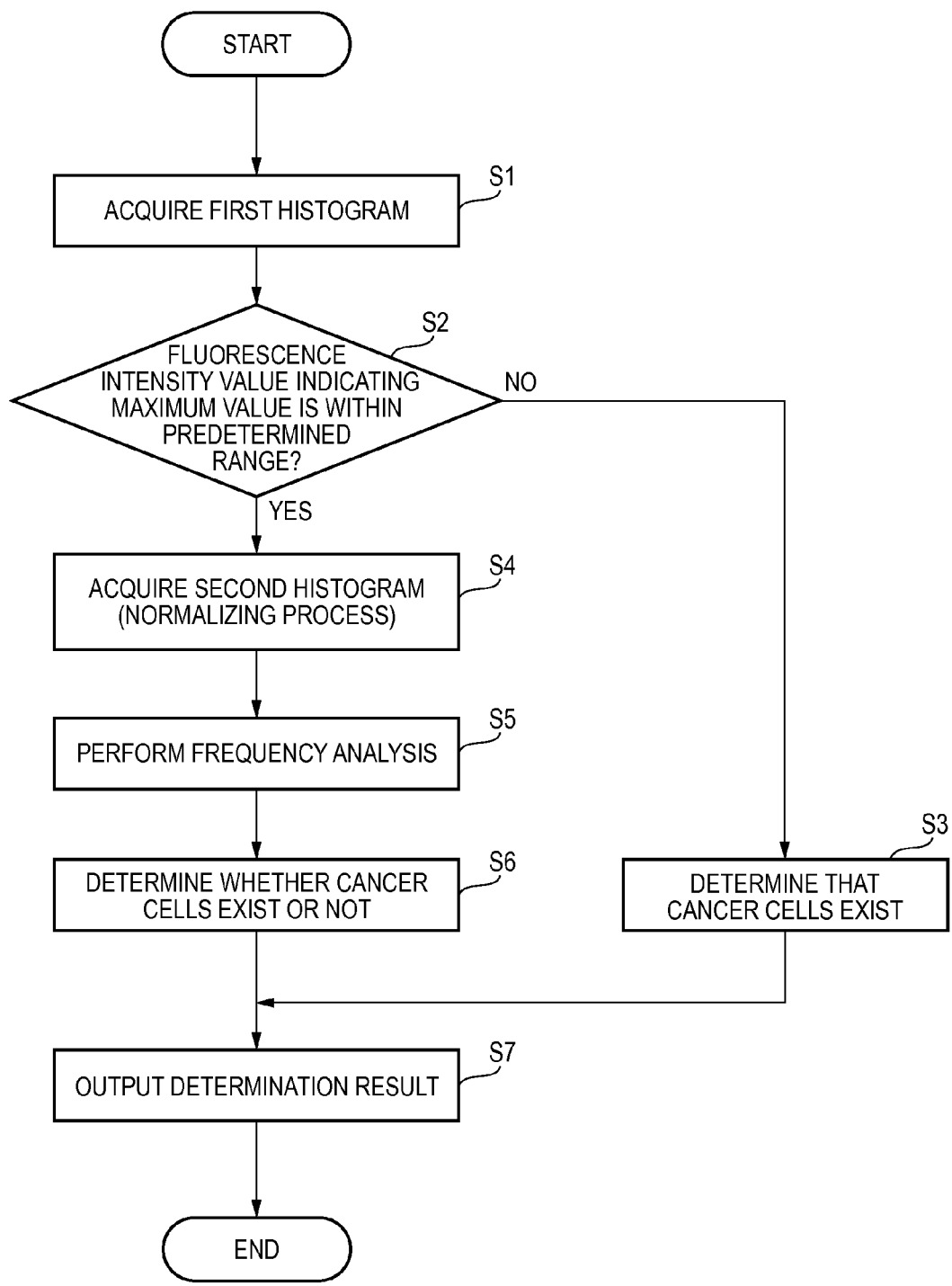
FIG. 6 is a flowchart showing a cell analyzing method of the embodiment of the presently disclosed subject matter.

FIG. 6 is a flowchart showing a method of determining whether cancerous cells exist or not, by using the thus configured cell analyzing apparatus 1.

First, the first histogram acquiring section 11 performs flow cytometry (step S1). As a result, the first histogram of fluorescence intensities is acquired by using a result of the measurement of the number of nuclear stained cells.

Next, the determining section 14 determines whether the fluorescence intensity value indicating the maximum value of the first histogram is within the predetermined range or not (step S2). If it is determined that the fluorescence intensity value is outside the predetermined range (No in step S2), the determining section 14 determines that cancer cells exist in the tissue to be analyzed. The determination result is output to the display device 2 through the outputting section 15 (step S3).

If the determining section 14 determines that the fluorescence intensity value indicating the maximum value of the first histogram is within the predetermined range (Yes in step S2), the second histogram acquiring section 12 acquires the second histogram which is normalized based on the fluorescence intensity value (step S4).

The term "normalized based on the fluorescence intensity value indicating the maximum value of the first histogram" means the normalization which has been described with reference to FIGS. 2A and 2B. Namely, normalization is performed so that the maximum value of the first histogram has a first predetermined value (1 in the examples of FIGS. 2A and 2B) (normalization in the ordinate direction), and further normalization is performed so that the fluorescence intensity value indicating the maximum value of the first histogram has a second predetermined value (200 in the examples of FIGS. 2A and 2B) (normalization in the abscissa direction).

Next, the analyzing section 13 performs the frequency analysis including the Fast Fourier Transform on the acquired second histogram (step S5). As a result, at least one index relating to the existence/nonexistence of cancer cells is acquired based on the plurality of parameters relating to the second histogram.

Then, the determining section 14 determines the existence/nonexistence of cancer cells based on the at least one index acquired by the frequency analysis (step S6). The result of the determination is output to the display device 2 through the outputting section 15 (step S7).

As described above, according to the cell analyzing apparatus 1 of the embodiment, the first histogram acquiring section 11 first acquires the first histogram of fluorescence intensities by using a result of the measurement of the number of nuclear stained cells, and the second histogram acquiring section 12 acquires the second histogram which is normalized based on the fluorescence intensity value indicating the maximum value of the first histogram. Here, normalization is performed so that the maximum value of the first histogram has the first predetermined value (normalization in the ordinate direction), and further normalization is performed so that the fluorescence intensity value indicating the maximum value of the first histogram has the second predetermined value (normalization in the abscissa direction). Therefore, the statistical dispersion of the shape of the second histogram which is acquired from every analysis object can be suppressed, and the existence/nonexistence of cancer cells can be determined on the same criterion. Consequently, cancer cells can be identified with higher accuracy.

In the cell analyzing apparatus 1 of the embodiment, moreover, in the case where the fluorescence intensity value corresponding to the maximum value of the first histogram is not within the predetermined range, and the existence/nonexistence of cancer cells is determined by the determining section 14 without performing the acquisition of the second histogram. Namely, the determining section 14 is configured so as to determine whether cancer cells exist or not, based on either one of the first and second histograms.

With respect to an analysis object for which the existence of cancer cells can be apparently determined, the determination is performed while omitting the acquisition of the second histogram. Therefore, the burden of the determining process can be suppressed, and the processing speed can be improved. When a first histogram in which the fluorescence intensity value corresponding to the maximum value is deviated from the predetermined range is normalized, the deviation from the shape of the second histogram which is originally assumed as the determination object is increased. When such an analysis object is excluded from the normalization objects, the effect of the normalization can be maximally ensured. Therefore, cancer cells can be identified with higher accuracy.

The cell analyzing apparatus 1 of the embodiment includes the analyzing section 13 which applies frequency analysis to the second histogram. The determining section 14 determines whether cancer cells exist or not, based on a result of the frequency analysis.

Since, as described above, the second histogram is normalized also with respect to the fluorescence intensity value, the frequency analysis can be applied under same conditions irrespective of the analysis object. Therefore, results which are obtained by the frequency analysis can be compared with each other under same conditions. Consequently, the effect of the frequency analysis can be maximally ensured, and cancer cells can be identified with higher accuracy.

In the cell analyzing apparatus 1 of the embodiment, the determining section 14 divides fluorescence intensity values of the second histogram into the plurality of zones SC1 to SC5 each of which corresponds to respective one of debris and a plurality of cancer cell cycles, and acquires an index relating to the existence/nonexistence of cancer cells for at least one of the plurality of zones SC1 to SC5. As described above, the second histogram is normalized also with respect to the fluorescence intensity value. Therefore, fluorescence intensity values each of which corresponds to respective one of the boundaries of the plurality of zones SC1 to SC5 are constant regardless of the acquired second histogram.

According to the configuration, as compared with the related art in which the plurality of zones are set in accordance with the shape of the acquired second histogram, the subjectivity of the determining person can be eliminated, and moreover the determination of the existence/nonexistence of cancer cells based on the setting of the plurality of zones can be automatized. Therefore, cancer cells can be identified with higher accuracy.

In the cell analyzing apparatus 1 of the embodiment, as described with reference to FIGS. 5A and 5B, the determining section 14 can acquire the plurality of indexes relating to the existence/nonexistence of cancer cells, based on the plurality of parameters relating to the second histogram, and determines the existence/nonexistence of cancer cells based on a combination of the plurality of indexes.

According to the configuration, the same second histogram can be multilaterally analyzed. Therefore, cancer cells can be identified with higher accuracy.

The embodiment has been described in order to facilitate understanding of the invention, and is not intended to limit the invention. It is a matter of course that the invention may be changed or improved without departing the spirit thereof, and includes equivalent embodiments.

In the embodiment, the analyzing section 13 performs the Fast Fourier Transform on the second histogram as frequency analysis, and acquires differential patterns of patterns which are obtained by the Fast Fourier Transform. The frequency analysis is not always required to include these two processes. The acquisition of differential patterns may be omitted depending on indexes to be acquired. When the existence/nonexistence of cancer cells can be determined from the second histogram itself, the frequency analysis may be omitted. Other useful examples of the frequency analysis are the Maximum Entropy Method, the Auto Regressive model, the Auto Regressive-Moving Average) model, the Short Time Fourier Transform, the Wavelet transform, and the Wigner distribution.

In the embodiment, the determination result which is obtained by the determining section 14, and which is output by the outputting section 15 is displayed by the display device 2 in an adequate manner. The determination result which is obtained by the determining section 14 is not always required to be displayed in a visible manner. The outputting section 15 may be connected to an adequate external apparatus to output a signal in a format corresponding to the external apparatus. Examples of the external apparatus are an audio outputting apparatus, a printer, and a data storage apparatus.

According to an aspect of the presently disclosed subject matter, there is provided a cell analyzing apparatus comprising: a first histogram acquiring section which is configured to acquire a first histogram of fluorescence intensities by using a result of a measurement of a number of nuclear stained cells; a second histogram acquiring section which is configured to acquire a second histogram that is normalized based on a fluorescence intensity value indicating a maximum value of the first histogram; a determining section which is configured to determine whether cancer cells exist or not, based on one of the first histogram and the second histogram; and an outputting section which is configured to output a result of the determination performed by the determining section.

According to an aspect of the presently disclosed subject matter, there is also provided a cell analyzing method comprising: acquiring a first histogram of fluorescence intensities by using a result of a measurement of a number of nuclear stained cells; in a case where a fluorescence intensity value indicating a maximum value of the first histogram is outside a predetermined range, determining that cancer cells exist; in a case where the fluorescence intensity value indicating the maximum value of the first histogram is within the predetermined range, acquiring a second histogram that is normalized based on the fluorescence intensity value, and determining whether the cancer cells exist or not; and outputting a result of the determination.

According to the configuration, in the acquisition of the second histogram, normalization is performed so that the maximum value of the first histogram has a first predetermined value (normalization in the ordinate direction), and further normalization is performed so that the fluorescence intensity value indicating the maximum value of the first histogram has a second predetermined value (normalization in the abscissa direction). Therefore, the statistical dispersion of the shape of the second histogram which is acquired from every analysis object can be suppressed, and the existence/nonexistence of the cancer cells can be determined on the same criterion. Consequently, the cancer cells can be identified with higher accuracy.

If the fluorescence intensity value indicating the maximum value of the first histogram is outside the predetermined range, it is possible to determine that cancer cells apparently exist. With respect to an analysis object for which the determination has been made, the acquisition of the second histogram may be omitted, whereby the burden of the determining process can be suppressed, and the processing speed can be improved. When a first histogram in which the fluorescence intensity value corresponding to the maximum value is deviated from the predetermined range is normalized, the deviation from the shape of the second histogram which is originally assumed as the determination object is increased. When such an analysis object is excluded from the normalization objects, the effect of the normalization can be maximally ensured. Therefore, the cancer cells can be identified with higher accuracy.

There may be further provided an analyzing section which is configured to apply frequency analysis to the second histogram, and the determining section may determine whether the cancer cells exist or not, based on a result of the frequency analysis. The frequency analysis may include Fast Fourier Transform.

Since, as described above, the second histogram is normalized also with respect to the fluorescence intensity value, the frequency analysis can be applied under same conditions irrespective of the analysis object. Therefore, results which are obtained by the frequency analysis can be compared with each other under same conditions. Consequently, the effect of the frequency analysis can be maximally ensured, and the cancer cells can be identified with higher accuracy.

The determining section may divide fluorescence intensity values of the second histogram into a plurality of zones each of which corresponds to respective one of debris and a plurality of cancer cell cycles, and acquire an index relating to existence/nonexistence of the cancer cells for at least one of the plurality of zones. As described above, the second histogram is normalized also with respect to the fluorescence intensity value. Therefore, fluorescence intensity values each of which corresponds to respective one of boundaries of the plurality of zones are constant regardless of the acquired second histogram.

According to the configuration, as compared with the related art in which the plurality of zones are set in accordance with the shape of the acquired second histogram, the subjectivity of the determining person can be eliminated, and moreover the determination of the existence/nonexistence of the cancer cells based on the setting of the plurality of zones can be automatized. Therefore, the cancer cells can be identified with higher accuracy.

The determining section may acquire a plurality of indexes relating to existence/nonexistence of the cancer cells, based on a plurality of parameters relating to the second histogram, and determine whether the cancer cells exist or not, based on a combination of the plurality of indexes.

According to the configuration, the same second histogram can be multilaterally analyzed. Therefore, cancer cells can be identified with higher accuracy.

What is claimed is:

1. A cell analyzing method comprising:
   acquiring a first histogram of fluorescence intensities by using a result of a measurement of a number of nuclear stained cells;
   determining whether the fluorescence intensity value indicating the maximum value of the first histogram is outside the predetermined range; in a case where a fluorescence intensity value indicating a maximum value of the first histogram is outside a predetermined range, determining that malignant tumor cells exist;
   in a case where the fluorescence intensity value indicating the maximum value of the first histogram is within the predetermined range, acquiring a second histogram that is normalized based on the fluorescence intensity value, and determining whether the malignant tumor cells exist or not; and
   outputting a result of the determination,
   wherein the acquiring the second histogram comprises performing normalization such that the maximum value of the first histogram has a first predetermined value and such that the fluorescence intensity value indicating the maximum value of the first histogram has a second predetermined value,
   wherein, when the fluorescence intensity value indicating the maximum value of the first histogram is determined to be outside the predetermined range, the determination that the malignant tumor cells exist is made without acquiring the second histogram, and
   wherein, when the fluorescence intensity value indicating the maximum value of the first histogram is determined to be within the predetermined range, the determination of whether the malignant tumor cells exist or not is made based on the second histogram.

2. The cell analyzing method according to claim 1, further comprising: an analyzing step in which frequency analysis is applied to the second histogram,
   wherein determining whether the malignant tumor cells exist or not is based on a result of the frequency analysis.

3. The cell analyzing method according to claim 2, wherein the frequency analysis includes Fast Fourier Transform.

4. The cell analyzing method according to claim 1, wherein the determining step comprises dividing fluorescence intensity values of the second histogram into a plurality of zones each of which corresponds to respective one of debris and a plurality of malignant tumor cell cycles, and acquiring an index relating to existence/nonexistence of the malignant tumor cells for at least one of the plurality of zones, and
   wherein fluorescence intensity values each of which corresponds to respective one of boundaries of the plurality of zones are constant regardless of the acquired second histogram.

5. The cell analyzing method according to claim 1, wherein the determining step comprises acquiring a plurality of indexes relating to existence/nonexistence of the malignant tumor cells, based on a plurality of parameters relating to the second histogram, and determining whether the malignant tumor cells exist or not, based on a combination of the plurality of indexes.

* * * * *